(12) United States Patent
Siravo et al.

(10) Patent No.: US 9,192,398 B2
(45) Date of Patent: Nov. 24, 2015

(54) ORTHOPEDIC IMPLANT INSERTION HANDLE AND AIMING GUIDE

(75) Inventors: Mark Siravo, East Norriton, PA (US); Glen Pierson, Glenmoore, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 2168 days.

(21) Appl. No.: 11/231,099

(22) Filed: Sep. 19, 2005

(65) Prior Publication Data

US 2007/0083213 A1   Apr. 12, 2007

(51) Int. Cl.
*A61B 17/58* (2006.01)
*A61B 17/17* (2006.01)
*A61B 17/00* (2006.01)

(52) U.S. Cl.
CPC ......... *A61B 17/1703* (2013.01); *A61B 17/1725* (2013.01); *A61B 2017/0046* (2013.01); *A61B 2017/00831* (2013.01); *A61B 2017/00915* (2013.01)

(58) Field of Classification Search
CPC .................................................. A61B 17/1703
USPC .............................................. 606/96–99, 104
See application file for complete search history.

(56) References Cited

U.S. PATENT DOCUMENTS

| | | | |
|---|---|---|---|
| 2,531,734 A | 11/1950 | Hopkins | |
| 3,613,684 A | 10/1971 | Sheridan | |
| 3,704,707 A | 12/1972 | Halloran | |
| 4,037,592 A | 7/1977 | Kronner | |
| 4,418,422 A | 11/1983 | Richter et al. | |
| 4,485,815 A | 12/1984 | Amplatz et al. | |
| 4,541,424 A | 9/1985 | Grosse et al. | |
| 4,621,628 A | 11/1986 | Brudermann | |
| 4,625,718 A | 12/1986 | Olerud et al. | |
| 4,722,336 A | 2/1988 | Kim et al. | |
| 4,803,976 A | 2/1989 | Frigg et al. | |
| 4,848,327 A | 7/1989 | Perdue | |
| 4,850,344 A | 7/1989 | Olerud et al. | |

(Continued)

FOREIGN PATENT DOCUMENTS

| | | |
|---|---|---|
| EP | 0 281 763 A2 | 9/1988 |
| EP | 0 495 488 A2 | 7/1992 |

(Continued)

OTHER PUBLICATIONS

International Search Report for International Application No. PCT/US06/036546, mailed Feb. 6, 2007.

(Continued)

*Primary Examiner* — Eduardo C Robert
*Assistant Examiner* — Stuart S Bray
(74) *Attorney, Agent, or Firm* — Fay Kaplun & Marcin, LLP

(57) ABSTRACT

An orthopaedic implant insertion instrument including an insertion handle and a radiolucent aiming guide and method of using same. The insertion handle may be formed of steel and is used for inserting an orthopaedic implant, such as an intramedullary nail or bone plate, into a patient. The radiolucent aiming guide is used to properly locate and guide a drill and/or other insertion instruments for installing fixation elements, such as screws, pins, nails, bolts, blades, etc., through the orthopaedic implant and into the affected bone to secure the implant in position and facilitate healing. The aiming guide is substantially hollow and tubular and is preferably formed of a carbon fiber material.

20 Claims, 3 Drawing Sheets

(56) References Cited

U.S. PATENT DOCUMENTS

| | | | |
|---|---|---|---|
| 4,865,025 A | 9/1989 | Buzzi et al. | |
| 4,877,019 A | 10/1989 | Vives | |
| 4,881,535 A | 11/1989 | Sohngen | |
| 4,917,111 A | 4/1990 | Pennig et al. | |
| 4,969,889 A | 11/1990 | Greig | |
| 4,976,713 A | 12/1990 | Landanger et al. | |
| 5,013,317 A | 5/1991 | Cole et al. | |
| 5,031,203 A | 7/1991 | Trecha | |
| 5,070,861 A | 12/1991 | Einars et al. | |
| 5,112,336 A | 5/1992 | Krevolin et al. | |
| 5,127,913 A | 7/1992 | Thomas, Jr. | |
| 5,141,513 A | 8/1992 | Fortune et al. | |
| 5,178,621 A | 1/1993 | Cook et al. | |
| 5,278,128 A | 1/1994 | Hotta et al. | |
| 5,283,808 A | 2/1994 | Cramer et al. | |
| 5,334,192 A | 8/1994 | Behrens | |
| 5,352,228 A | 10/1994 | Kummer et al. | |
| 5,403,321 A * | 4/1995 | DiMarco | 606/96 |
| 5,403,322 A | 4/1995 | Herzenberg et al. | |
| 5,411,503 A | 5/1995 | Hollstien et al. | |
| 5,417,688 A | 5/1995 | Elstrom et al. | |
| 5,426,687 A | 6/1995 | Goodall et al. | |
| 5,433,720 A | 7/1995 | Faccioli et al. | |
| 5,458,599 A | 10/1995 | Adobbati | |
| 5,478,329 A | 12/1995 | Ternamian | |
| 5,478,343 A | 12/1995 | Ritter | |
| 5,513,240 A | 4/1996 | Hausmann et al. | |
| 5,514,145 A | 5/1996 | Durham et al. | |
| 5,540,691 A | 7/1996 | Elstrom et al. | |
| 5,540,695 A | 7/1996 | Levy | |
| 5,584,838 A | 12/1996 | Rona et al. | |
| 5,620,449 A | 4/1997 | Faccioli et al. | |
| 5,630,805 A | 5/1997 | Ternamian | |
| 5,658,283 A | 8/1997 | Huebner | |
| 5,665,086 A | 9/1997 | Itoman et al. | |
| 5,707,375 A | 1/1998 | Durham et al. | |
| 5,722,978 A | 3/1998 | Jenkins, Jr. | |
| 5,728,128 A | 3/1998 | Crickenberger et al. | |
| 5,766,179 A | 6/1998 | Faccioli et al. | |
| 5,772,594 A | 6/1998 | Barrick | |
| 5,891,158 A | 4/1999 | Manwaring et al. | |
| 5,976,134 A | 11/1999 | Huebner | |
| 6,001,097 A | 12/1999 | Campopiano et al. | |
| 6,036,657 A | 3/2000 | Milliman et al. | |
| 6,036,696 A | 3/2000 | Lambrecht et al. | |
| 6,106,528 A | 8/2000 | Durham et al. | |
| 6,129,729 A | 10/2000 | Snyder | |
| 6,168,595 B1 | 1/2001 | Durham et al. | |
| 6,214,013 B1 | 4/2001 | Lambrecht et al. | |
| 6,371,959 B1 | 4/2002 | Trice | |
| 6,635,061 B1 | 10/2003 | Snyder | |
| 6,656,189 B1 * | 12/2003 | Wilson et al. | 606/97 |
| 6,869,434 B2 | 3/2005 | Choi | |
| 2002/0058948 A1 | 5/2002 | Arlettaz | |
| 2002/0151897 A1 | 10/2002 | Zirkle, Jr. | |
| 2003/0220651 A1 | 11/2003 | Pusnik et al. | |
| 2004/0059329 A1 * | 3/2004 | Zander | 606/53 |
| 2004/0082959 A1 * | 4/2004 | Hayes et al. | 606/96 |
| 2004/0167533 A1 | 8/2004 | Wilson et al. | |
| 2004/0215204 A1 | 10/2004 | Davison et al. | |
| 2005/0015092 A1 * | 1/2005 | Rathbun et al. | 606/96 |
| 2005/0065532 A1 | 3/2005 | Honl et al. | |
| 2005/0070903 A1 | 3/2005 | Roth et al. | |
| 2005/0075562 A1 | 4/2005 | Szakelyhidi, Jr. et al. | |
| 2006/0200160 A1 * | 9/2006 | Border et al. | 606/88 |

FOREIGN PATENT DOCUMENTS

| | | |
|---|---|---|
| EP | 1 344 494 A2 | 9/2003 |
| EP | 1 449 484 A1 | 8/2004 |
| EP | 1 486 176 A1 | 12/2004 |
| FR | 2 713 914 A1 | 6/1995 |
| WO | WO 95/30378 A1 | 11/1995 |
| WO | WO 03/092515 A2 | 11/2003 |

OTHER PUBLICATIONS

Written Opinion of the International Search Authority for International Application No. PCT/US06/036546.

* cited by examiner

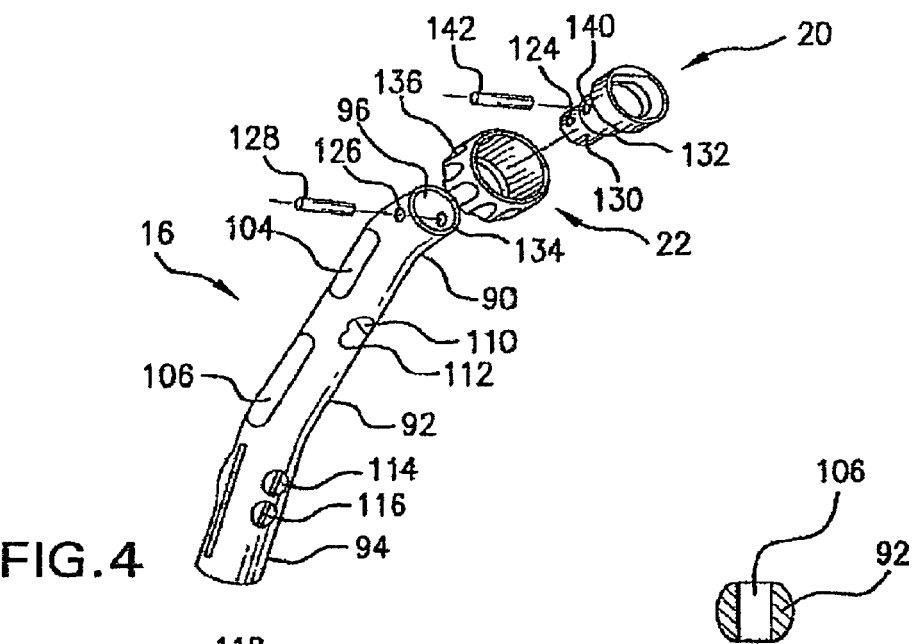
FIG. 4
FIG. 6
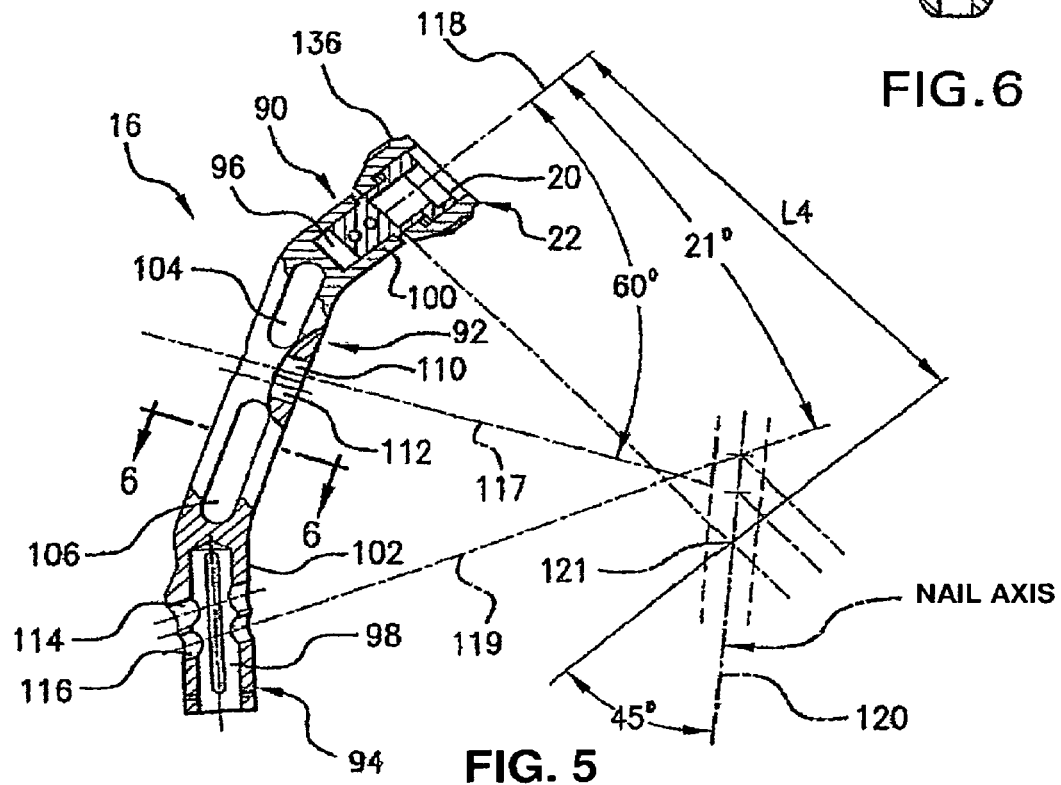
FIG. 5

ORTHOPEDIC IMPLANT INSERTION HANDLE AND AIMING GUIDE

TECHNICAL FIELD

The present invention relates to an orthopedic implant insertion instrument, and more particularly, to an implant insertion handle and aiming guide that is radiolucent and may be exceedingly useful for the insertion of orthopaedic implants, such as intramedullary nails or bone plates, and for fixing an implant relative to a patient's bone with accurately placed bone fixation elements, e.g., screws.

BACKGROUND OF THE INVENTION

Fractured or deformed long bones, e.g., femur, tibia, are typically repaired, reconstructed and/or healed using an elongated rod, often referred to as a "nail," which is inserted into the intramedullary canal of the bone. Once inserted, there is a need to stabilize bone segments or parts relative to the nail or rod to enhance the healing, repair and/or reconstruction process. To this end, intramedullary nails may have one or more transverse holes, which may be formed perpendicular to the long axis of the nail and/or at an angle relative to the long axis of the nail, for the passage of bone screws, nails, bolts, pins or other fixation elements that traverse the lateral cortex of the femur and may pass through the femoral neck and into the femoral head. Other fixation elements may pass through the nail and the shaft of the femur to prevent unwanted rotation or translation of the nail.

During such a surgical procedure, a surgeon will continually monitor the location of the implants within the bone by using a fluoroscope. Fluoroscopy allows the surgeon to see the locations of the femur, the nail in the femur, and any transverse fixation elements being installed. The surgeon is then able to aim a drill and to correctly insert the fixation elements, e.g., screws, into the nail holes at the desired femur locations.

Existing targeting devices for orthopedic implants are frequently described as being radio-transparent or radiolucent, however, they are sufficiently dense or thick-walled to cause scattering of the radiation being used. Frequently this is caused by the material being used, but is also caused by the configuration of the structure of the device. X-ray scattering compromises accuracy by detracting from the clarity of the operative site, which may make the operative procedure longer and more difficult.

SUMMARY OF THE INVENTION

The present invention generally relates to an orthopaedic implant insertion tool, and, in particular, an implant insertion handle and aiming guide having improved radiolucent properties. The present invention also relates to a method for inserting and restraining an orthopedic implant.

In one embodiment, the orthopedic implant insertion handle and aiming guide may comprise an insertion handle, which may be formed of steel, titanium, or other suitable material, and a thin walled, hollow aiming guide arm connected to the insertion handle where the guide arm may be formed of carbon fiber or other suitable radiolucent material and has at least one transverse bore extending therethrough. The guide arm may be formed as a tube of substantially circular or polygonal cross-section. Preferably, the guide arm is removably connected to said insertion handle, but the guide arm may be formed integral with the insertion handle. The aiming guide may further include a first end portion, a second end portion and a substantially linear middle portion located between the first and second end portions, and the first end portion may form an angle with respect to the middle portion. The first end portion of the aiming guide may have a wall thickness greater than the wall thickness of the middle portion.

In another embodiment, the orthopedic implant insertion handle and aiming guide may comprise a coupling connected to the aiming guide arm and a threaded coupling nut mounted to the coupling enabling the guide arm to be removably connected to the insertion handle.

In still another embodiment, a pin may be mounted to the coupling, and the insertion handle may include a notch such that when connecting the guide arm and the insertion handle, the guide arm is precisely aligned and positioned in relation to an implanted intramedullary nail or plate. Drilling into a bone and inserting screws in the bone are thereby facilitated.

In still another embodiment, the insertion handle may be used independently of the guide arm to install an intramedullary nail or plate and thereafter, the guide arm may be connected to the insertion handle to guide screws into the nail or plate and into the femur in which the nail or plate is implanted.

BRIEF DESCRIPTION OF THE DRAWINGS

To facilitate an understanding of and for the purpose of illustrating the present invention, exemplary and preferred features and embodiments are disclosed in the accompanying drawings, it being understood, however, that the invention is not limited to the precise arrangements and instrumentalities shown, and wherein similar reference characters denote similar elements throughout the several views, and wherein:

FIG. 4 is an exploded isometric view of a guide arm, a coupling and a coupling nut of the present invention.

FIG. 5 is a partially sectional elevation view of the guide arm, the coupling and the coupling nut shown in FIG. 4.

FIG. 6 is sectional view taken along line 6-6 of FIG. 5.

DETAILED DESCRIPTION

For the purposes of promoting an understanding of the principles of the invention, reference will now be made to an exemplary, non-limiting embodiment illustrated in the figures and specific language will be used to describe the same. It will nevertheless be understood that no limitation of the scope of the invention is hereby intended, such alterations and further modifications, and such further applications of the principles of the invention as illustrated herein being contemplated as would normally occur to one skilled in the art to which the invention relates. In this regard, exemplary features may be shown and described which are not required to carry out the invention and thus it is intended that the invention only be limited by the claims.

Figure 1:
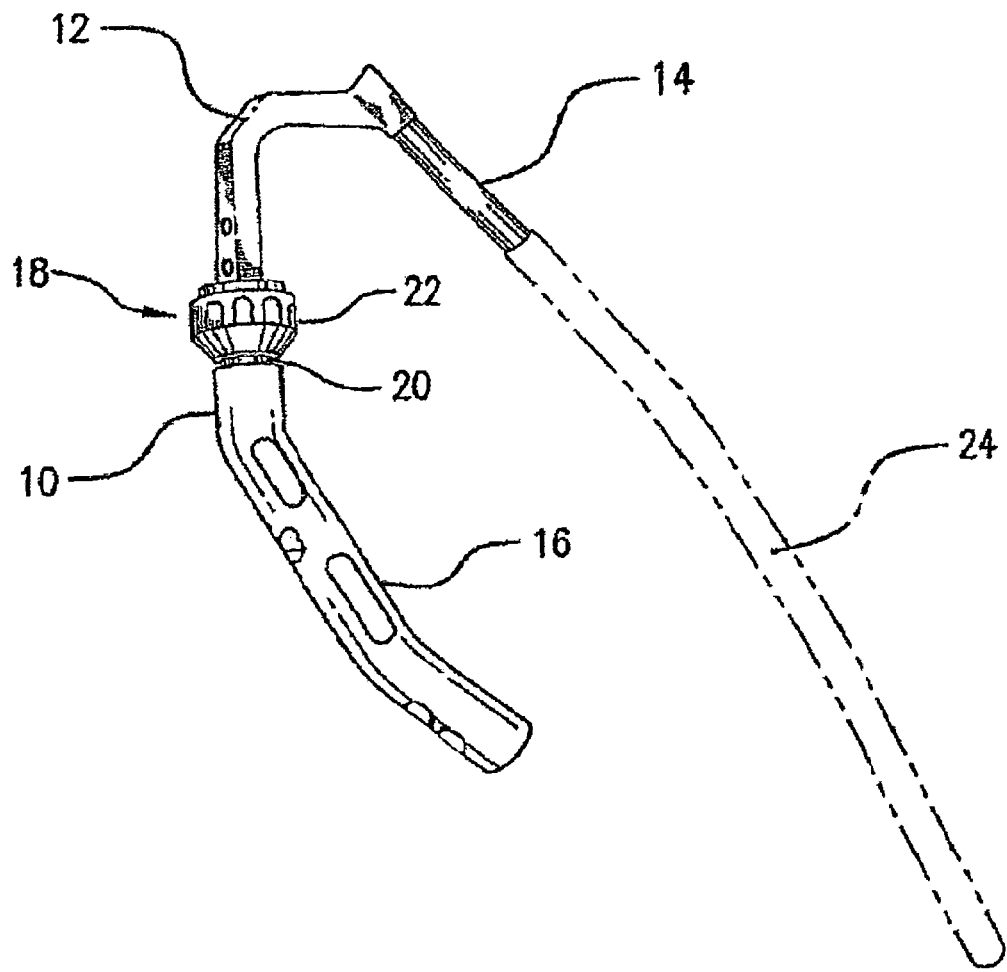
FIG. 1 is an isometric view of the radiolucent orthopedic implant insertion and aiming guide of the present invention.

As shown in FIG. 1, the radiolucent orthopedic implant insertion handle and aiming guide 10 is a surgical instrument that may be used first to insert an intramedullary nail into the intramedullary canal of a patient's long bone, such as a femur or a tibia, in order to stabilize fractures and to act as a guide for aiming a drill to enable the insertion of transverse fixation elements, such as screws, nails, blades, bolts, etc., into the long bone and through openings in the intramedullary nail to lock the device in place. The guide may also be used to manipulate and to remove orthopedic implants, such as the nail, and to implant plates. The guide may include an insertion handle or base 12, a barrel 14, a guide arm 16 and a connecting structure 18 that may include a coupling 20 and a threaded coupling nut 22. An intramedullary nail 24 is illustrated in phantom line connected to the barrel 14.

Figure 2:
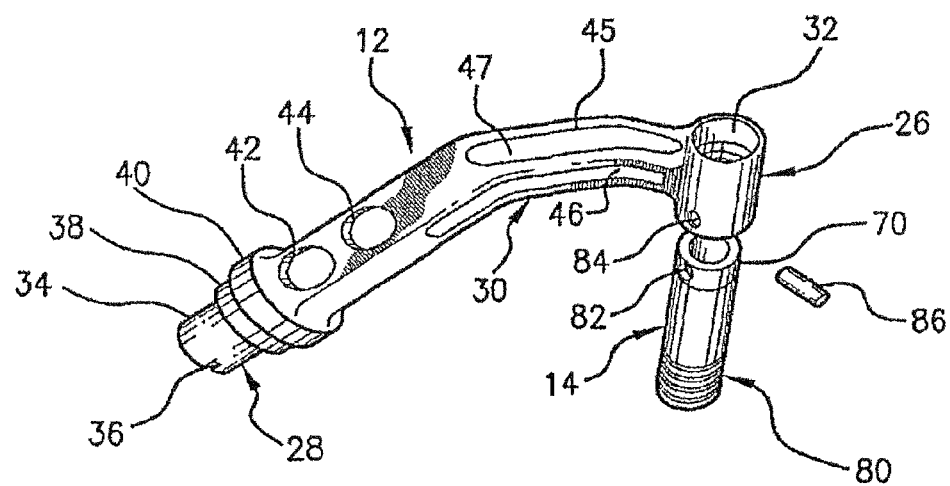
FIG. 2 is an isometric view of an insertion handle and a barrel of the inventive guide.
Figure 3:
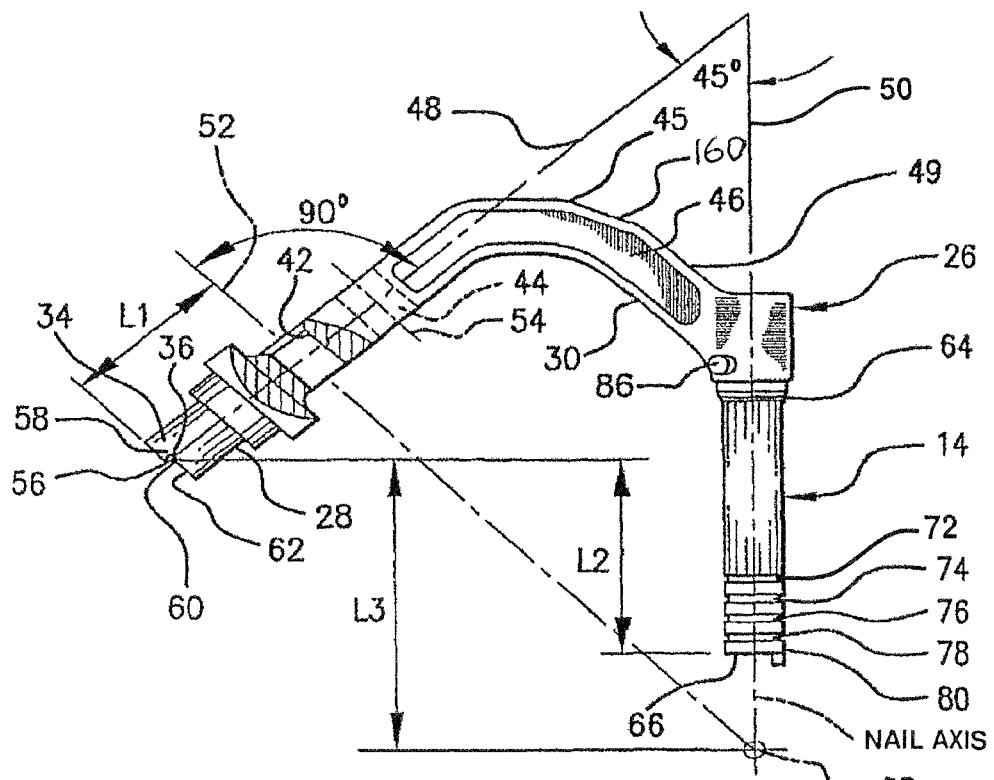
FIG. 3 is a partially sectional elevation view of the insertion handle and the barrel shown in FIG. 2.

Referring to FIGS. 2 and 3, the insertion handle 12 may have a proximal end portion 26, a distal end portion 28 and a middle portion 30. The proximal end portion 26 may include a bore 32 for receiving and securing the barrel 14. The barrel 14 may in turn support the intramedullary rod or nail 24 which may be used to stabilize and heal an injured or deformed bone, e.g., femur, tibia, etc.

The distal end portion 28 may include a guide arm insertion section 34 having a notch 36, a collar section 38 and an annular threaded shoulder section 40. The insertion section 34, the collar section 38 and the shoulder section 40 may be part of the connecting structure 18 and operatively connect to the coupling 20 and the threaded coupling nut 22 to enable the insertion handle 12 to be removably secured to the guide arm 16. As will be explained in more detail below, the notch 36 prevents rotation of the guide arm, and the collar section 38 acts as a positioning guide when mounting the guide arm. Shoulder section 40 threadedly engages with the coupling nut 22 to position and secure the guide arm to the insertion handle. The distal end portion 28 may also include two drill receiving holes 42, 44 positioned close to the shoulder section 40. In some embodiments, either or both of holes 42, 44 may be threaded for receiving other insertion instruments (not shown). It should also be noted that, in alternate embodiments, the insertion handle and guide arm may be formed as a single unit.

The middle portion 30 of the insertion handle is formed integral with the proximal and distal end portions 26, 28 and may be configured with the proximal and distal end portions in a generalized "L" shape. An upper flat surface 45 may be used as a hammer strike surface to facilitate the insertion of the nail. Side and top grooves 46, 47 may be formed in the middle portion. Another side groove, not shown, may be formed opposite the side groove 46. The grooves provide for a lighter instrument.

As illustrated in FIG. 3, a central axis 48 of distal end portion 28 may be about 45 degrees away from a central axis 50 of the bore 32 of the proximal end portion 26. The central axis 50 is also coincident with an axis of the nail. A central axis 52 of the drill receiving opening 42 may be about 90 degrees from the center axis 48. A central axis 54 of the drill receiving opening 44 may be about 90 degrees from the distal end central axis 48.

A measurement point 56, which is the center of a 6 mm circle placed in the notch 36 to represent a pin to be described below, is positioned to be tangent to two walls 58, 60 that meet at an angle of about 100 degrees. The vertex of the notch may be 3 mm from an end surface 62 of the distal end portion 28. The distance L1 between the point 56 and the central axis 52 may be on the order of about 40 mm, and in one specific embodiment is about 42.9 mm. The distance from the central axis 54 to the point 56 may be on the order of 65 mm, and the distance from the central axis 50 to the point 56 may be on the order of 135 mm. The outer diameter of the insertion section 34 of distal end portion 28 may be about 16 mm, the inner diameter of the insertion section 34 may be about 14 mm, the vertical distance (as shown in FIG. 3) from the point 56 to an end surface 64 of the proximal end portion 26 may be about 20 mm, the diameter of the drill receiving hole 44 may be about 12 mm, the diameter of the drill receiving hole 42 may also be about 12 mm and the vertical distance L2 from the point 56 to an end surface 66 of the barrel 14 may be about 54 mm. The vertical distance L3 from a point 68 on the central axis 50 to the point 56 may be about 75 mm. These measurements are illustrated in FIG. 3. The angular relationship between the distal end central axis 48 and the flat surface 45 may be about 45°, the angle between the flat surface 45 and the surface 160 may be about 20° and the angle between the flat surface 45 and the surface 49 may be about 40°.

The barrel 14 may have a tubular design including a slightly enlarged head portion 70 and a series of four circumstantial grooves 72, 74, 76, 78 at a base portion 80 of the barrel. The head portion 70 is constructed to fit within the proximal end portion bore 32 until an internal stop is reached. A laterally directed fastener receiving opening 82 may be formed in the barrel head portion 70 and a similar fastener receiving, laterally directed opening 84 may be formed in the proximal end portion 26 of the insertion handle 12 such that when the barrel is inserted into the proximal end portion 26 of the insertion handle and the openings 82 and 84 are aligned, a fastener, which may be in the form of a pin 86, may be inserted to lock the aligned barrel in place. The barrel 14 may also include a tab for aligning the nail.

The material of the insertion handle may be steel or any other strong, suitable material. The length of the barrel 14 may be on the order of 90 mm, the outer diameter of the head portion 70 may be on the order of 14 mm, the remainder of the barrel may have an outer diameter of about 13 mm and the barrel may have an inner diameter of about 8 mm. The grooves 72, 74, 76, 78 may be located 22.4, 17.4, 12.4 and 7.4 mm, respectively, from the end surface 66 of the barrel, and each may have a width of 0.8 mm and a depth of about 0.5 mm.

Referring now to FIGS. 4-6, the guide arm 16 is shown in detail and may include an upper end portion 90, a middle portion 92 and a lower end portion 94. The upper end portion 90 and the lower end portion 94 are generally tubular with open centers 96, 98 and thin walls 100, 102. The middle portion has a greatly reduced cross section formed by two lateral pass-through slots 104, 106. The open center 96 of the upper end portion 90 may have a diameter of about 16.99 mm and a length of about 23 mm to receive the coupling 20. The open center 98 of the lower end portion may have a diameter of about 16 mm and a length of about 70 mm. The outer diameter of the upper end portion 90 may be about 25 mm forming a thin wall of about 4 mm in thickness. The lower end portion 94 may have a partial thin wall of about 4.5 mm and a thicken portion building to a little more than twice the thickness to facilitate aligning drills through the adjacent drill guide bores. The pass-through slots 104, 106 may be about 12 mm wide, with the slot 104 having a length of about 38 mm and the slot 106 having a length of about 54 mm.

The middle portion 92 of the guide arm 16 may be offset from the upper portion 90 by an angle of approximately 28 to 32 degrees. The lower portion 94 may be offset from the upper portion 90 by angle of about 50 to 54 degrees.

A first or upper pair of drill guide bores or openings 110, 112 may be formed in the middle portion 92 of the guide arm 16 between the slots 104, 106, and a second or lower pair of drill guide bores or openings 114, 116 may be formed in the lower end portion 94. The first pair of drill guide bores 110, 112 may have central axes, such as the central axis 117, located approximately 60 degrees from a central axis 118 of the upper end portion 90 of the guide arm. The second pair of drill guide bores 114, 116 may have central axes, such as the central axis 119, at an angle of approximately 21 degrees from the central axis 118 of the upper end portion 90 of the guide arm. Shown in phantom line in FIG. 5 is a nail axis 120 which may be at an angle of about 45 degrees from the central axis 118 of the upper end portion 90 and spaced from the axis 118 at a point 121 by a distance L4 on the order of 190 mm. The lower bores 114, 116 may have diameters on the order of between 9 and 12 mm, and preferably 11.5 mm, and having axes spaced about 13 mm apart. The upper bores 110, 112 may have overlapping diameters of between about 9 and 13 mm, and preferably about 12 mm, and have axes spaced about 7 mm apart.

The material of the guide arm 16 is carbon fiber which has improved radiolucent qualities especially when combined with the thin walls 100, 102, the hollow open centers 96, 98 and the pass-through slots 104, 106 disclosed above.

The coupling 20 and the coupling nut 22 may be inserted in the upper end portion 90 of the guide arm 16 as shown in FIG. 5. A first or lower fastener receiving opening 124 is formed in the coupling. A similar fastener receiving opening 126 may also be formed in the upper end portion 90 of the guide arm 16. The coupling 20 may be press fitted into the guide arm 16, and the fastener receiving openings 124, 126 may be aligned to receive a pin 128 which locks the aligned coupling 20 to the upper end portion 90 of the guide arm 16. The coupling 20 may include a lower shoulder 130, and an upper shoulder 132. The lower shoulder abuts an end surface 134 of the guide arm 16 and the coupling upper shoulder 132 provides an abutment for the coupling nut 22. The coupling nut 22 is positioned around the coupling 20. The coupling nut engages the annular shoulder 40 of the insertion handle 12. The coupling nut includes an outer ribbed surface 136 to facilitate rotation and tightening of the nut on the insertion arm annular shoulder 40.

A second or upper fastener receiving opening 140 may be formed in the coupling. A pin 142 inserted in the upper pin receiving opening 140 acts as a positioning stop to the insertion handle 12 by engaging the notch 36 of the distal end portion 28 of the insertion handle 12. The pin 142 also causes the proper alignment of the guide arm 16 and the insertion handle 12. The central axis of the pin 142 is coincident with the point 56, FIG. 3.

In operation, an orthopedic implant, such as a femoral or tibial intramedullary nail 24, is installed using the insertion handle 12. Because the insertion handle is formed of a strong, durable material, e.g., stainless steel, titanium, etc., a large amount of force, including hammer blows, may be used without any concern about damaging the insertion handle. Thereafter, the hollow guide arm 16, which may be relatively weak when compared to the insertion handle, may be connected to the insertion handle 12 by engaging the threaded coupling nut 22 with the annular shoulder portion 40 of the insertion handle. Because relative rotation of the guide arm 16 and coupling 20 may be prevented by use of the pin 128 in the fastener receiving openings 124, 126, and because the notch 36 of the insertion handle may be seated on the pin 142, the drill guiding bores 110, 112, 114, 116 in the guide arm 16 and the drill guide bores 42, 44 in the insertion handle 12 may be aligned with openings (not shown) in the nail. Thereafter, a surgeon is in position to use the drill guiding bores to aim and insert fixation elements, such as screws, pins, nails, blades or bolts, so that an injured or deformed bone may be immobilized.

To ensure that the drilling and/or insertion of fixation elements, such as a screw, is properly aligned, the limb of the patient may be subjected to x-rays thereby giving the surgeon a clear picture of the bone, the nail, the inserting drill bit and the fixation element. To keep radiation interference to a minimum, the guide arm 16 is formed of thin walled carbon fiber in the form of a thin walled tube in its upper and lower end portions and a substantially reduced cross sectional area in it middle portion.

In embodiments where the insertion handle/aiming guide is configured as two connectable and detachable pieces, rather than a one-piece design, a surgeon may be able to exert a larger insertion force on the intramedullary nail or plate when using the insertion handle 12 separated from the aiming guide. When the nail or plate is in place, the guide arm 16 may be easily, quickly and accurately engaged to the insertion handle. Thereafter, the drilling or installation of fixation elements, e.g., screws, pins, nails, blades, bolts, etc., may be performed easily and accurately without the application of excessive force. Hence, a thin or small section of radiolucent carbon fiber may be conveniently used. As discussed above, in other embodiments, the insertion handle/aiming guide may be configured as a one piece design.

It should be noted that there are various sizes and types of intramedullary nails used in orthopaedic surgery, e.g., solid, cannulated, femoral, humeral, tibial, etc. Therefore, the exact dimensions and angles disclosed above are not to be considered limiting in any way. Moreover, the present invention may be adapted for use with other orthopaedic implants and devices, such as bone plates, spinal implants, etc.

The present invention has been described in connection with the preferred embodiment. The embodiment, however, is merely for example and the invention is not restricted thereto or limited thereby. Thus, it will be understood by those skilled in the art that other variations and modifications can easily be made within the scope of the invention as defined by the appended claims, thus it is only intended that the present invention be limited by the following claims.

The invention claimed is:

1. A radiolucent orthopedic implant insertion instrument comprising:
   an insertion handle including a proximal end configured to couple to a distal end of an orthopedic implant; and
   an aiming guide including a proximal end configured to couple to a distal end of the insertion handle so that the aiming guide extends distally therefrom, the aiming guide being formed as a substantially hollow structure of radiolucent material and having a plurality of transverse bores formed therethrough, the transverse bores being positioned and oriented so that, when the insertion handle is coupled to an implant and to the aiming guide, the transverse bores align with a target feature of the implant in such a way that axes of the transverse bores intersect the target feature and each respective transverse bore without intersecting a surface of any of the transverse bores, wherein the transverse bores have overlapping diameters.

2. The instrument of claim 1, wherein the aiming guide is a tube of substantially circular cross-section.

3. The instrument of claim 1, wherein the aiming guide is a tube of polygonal cross section.

4. The instrument of claim 1, wherein the aiming guide has an open cross-section.

5. The instrument of claim 1, wherein the aiming guide is removably connectable to the insertion handle.

6. The instrument of claim 5, wherein the aiming guide is formed of carbon fiber.

7. The instrument of claim 5, further comprising a coupling and a threaded coupling nut a first end of which engages one of the proximal end of the aiming guide and the distal end of the insertion handle, a second end of the coupling nut including an internal thread for engaging a threaded surface on the other of the distal end of the insertion handle and the proximal end of the aiming guide to secure the insertion handle to the aiming guide.

8. The instrument of claim 7, wherein the proximal end of the aiming guide includes an opening sized and shaped to slidably receive therein a distal end of a coupling, a proximal end of the coupling being coupled to the distal end of the insertion handle when in an operative configuration, the threaded portion being formed on the insertion handle proximally of the distal end thereof which is coupled to the coupling, the aiming guide further including a fastener receiving opening-which, when the distal end of the coupling is received within the proximal end of the aiming guide in a desired orientation, aligns with a fastener receiving bore extending through the distal end of the coupling.

9. The instrument of claim 1, wherein proximal and distal portions of the aiming guide are angled with respect to a substantially linear middle portion thereof.

10. The instrument of claim 9, wherein the distal portion of the aiming guide has a first wall thickness and the proximal portion of the aiming guide has a second wall thickness, and the first wall thickness being greater than the second wall thickness.

11. The instrument of claim 10, wherein the first wall thickness is approximately 4.5 mm and the second wall thickness is approximately 4 mm.

12. The instrument of claim 1, wherein the insertion handle includes at least one bore for aligning a drill.

13. The instrument of claim 1, wherein the insertion handle is formed of stainless steel, titanium, or titanium alloy.

14. A radiolucent orthopedic implant insertion instrument comprising:
   an insertion handle having a proximal portion configured and dimensioned for removable connection to a distal portion of an orthopaedic implant; and
   an aiming guide formed as a substantially hollow structure of radiolucent material and having a plurality of transverse bores formed therethrough, the aiming guide having a proximal portion configured and dimensioned for connection to a distal end of the insertion handle so that the aiming guide extends distally therefrom, a distal portion and a substantially linear middle portion disposed between the proximal and distal portions, wherein the proximal and distal portions are substantially tubular, wherein when the insertion handle is coupled to an implant and to the aiming guide, the transverse bores align with a respective target feature of the implant in such a way that axes of the transverse bores intersect the respective target feature and the transverse bores without intersecting a surface of any of the transverse bores, wherein the transverse bores have overlapping diameters.

15. The instrument of claim 14, wherein the aiming guide is formed of carbon fiber.

16. The instrument of claim 15, wherein the distal portion has a first wall thickness and the proximal portion has a second wall thickness, and the first wall thickness is being greater than the second wall thickness.

17. The instrument of claim 15, wherein the middle portion of the aiming guide has at least one linear slot formed therethrough.

18. The instrument of claim 15, wherein the transverse bores are configured for locating and aligning a drill or implant insertion tool.

19. The instrument of claim 15, wherein one of the distal end of the insertion handle and the proximal end of the aiming guide includes and a threaded coupling nut and the other of the distal end of the insertion handle and the proximal end of the aiming guide includes a threaded portion configured and dimensioned to be secured within the coupling nut to secure the insertion handle to the aiming guide.

20. The instrument of claim 19, wherein the proximal end of the aiming guide includes an opening sized and shaped to slidably receive therein a distal end of a coupling, a proximal end of the coupling being coupled to the distal end of the insertion handle when in an operative configuration, the threaded portion being formed on the insertion handle proximally of the distal end thereof which is coupled to the coupling, the proximal portion of the aiming guide further including which, when the distal end of the coupling is received within the proximal end of the aiming guide in a desired orientation, aligns with a fastener receiving bore extending through the distal end of the coupling.

* * * * *

UNITED STATES PATENT AND TRADEMARK OFFICE
CERTIFICATE OF CORRECTION

PATENT NO.        : 9,192,398 B2
APPLICATION NO.   : 11/231099
DATED             : November 24, 2015
INVENTOR(S)       : Siravo et al.

Page 1 of 1

It is certified that error appears in the above-identified patent and that said Letters Patent is hereby corrected as shown below:

IN THE CLAIMS

Claim 16, Column 8, Line 15:
"second wall thickness, and the first wall thickness is being" should read "second wall thickness, and the first wall thickness being".

Claim 19, Column 8, Line 25:
"guide includes and a threaded coupling nut and the other of" should read "guide includes a threaded coupling nut and the other of".

Signed and Sealed this
Fifth Day of April, 2016

Michelle K. Lee
*Director of the United States Patent and Trademark Office*